United States Patent
Böde

(10) Patent No.: US 10,245,219 B2
(45) Date of Patent: Apr. 2, 2019

(54) METHOD FOR THE REMOVAL OF TATTOOS AND SKIN DISCOLOURATION

(71) Applicant: Klaus Böde, Frankfurt (DE)

(72) Inventor: Klaus Böde, Frankfurt (DE)

(*) Notice: Subject to any disclaimer, the term of this patent is extended or adjusted under 35 U.S.C. 154(b) by 580 days.

(21) Appl. No.: 14/581,657

(22) Filed: Dec. 23, 2014

(65) Prior Publication Data

US 2016/0175211 A1    Jun. 23, 2016

(51) Int. Cl.
| | |
|---|---|
| *A61K 8/14* | (2006.01) |
| *A61K 8/365* | (2006.01) |
| *A61B 17/32* | (2006.01) |
| *A61Q 1/14* | (2006.01) |
| *A61B 17/3209* | (2006.01) |
| *A61B 17/322* | (2006.01) |
| *A61B 17/00* | (2006.01) |
| *A61M 37/00* | (2006.01) |

(52) U.S. Cl.
CPC .............. *A61K 8/365* (2013.01); *A61B 17/32* (2013.01); *A61B 17/322* (2013.01); *A61B 17/3209* (2013.01); *A61K 8/14* (2013.01); *A61Q 1/145* (2013.01); *A61B 2017/00769* (2013.01); *A61K 2800/91* (2013.01); *A61M 37/0076* (2013.01); *A61M 37/0084* (2013.01); *A61M 2210/04* (2013.01)

(58) Field of Classification Search
CPC ........... A61B 2017/00769; A61B 2017/00747; A61B 2017/00752; A61B 2017/00756; A61B 2017/00761; A61B 17/205; A61M 37/0076; A61M 37/0084; A61M 2210/04
See application file for complete search history.

(56) References Cited

U.S. PATENT DOCUMENTS

| | | | |
|---|---|---|---|
| 8,663,162 B2 | 3/2014 | Bunting et al. | |
| 2009/0324705 A1* | 12/2009 | Vikhrieva | A61K 9/0014 |
| | | | 424/450 |

FOREIGN PATENT DOCUMENTS

| | | | | |
|---|---|---|---|---|
| JP | 2003339875 A | * | 12/2003 | |
| WO | WO 2006096998 A1 | * | 9/2006 | ............... A61K 8/06 |
| WO | WO 2012099563 A1 | * | 7/2012 | ............... A45D 34/04 |

OTHER PUBLICATIONS

Patent translate: Translation of JP 2003339875 A, Jan. 13, 2016.*
Patent translate: Translation of WO 2006096998 A1, Jan. 13, 2016.*

* cited by examiner

*Primary Examiner* — Bradley J Osinski
*Assistant Examiner* — Nilay J Shah
(74) *Attorney, Agent, or Firm* — Lee & Hayes, P.C.

(57) ABSTRACT

A method for the removal of tattoos or skin discoloration includes applying a removal fluid to the skin using a pigmentation device or a knife, such that the removal fluid is applied by small-scale, partial removal of the epidermis. In addition, the disclosure involves a removal fluid for use in the method.

18 Claims, 1 Drawing Sheet

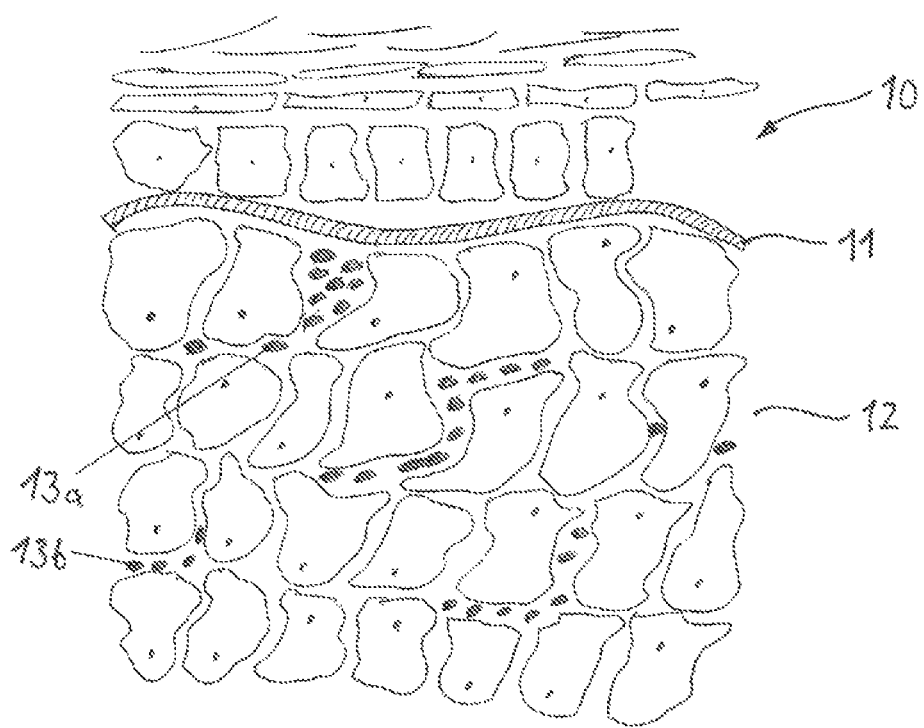

METHOD FOR THE REMOVAL OF TATTOOS AND SKIN DISCOLOURATION

BACKGROUND

The invention concerns a method for the removal of tattoos and skin discolouration as well as a removal fluid for use in this method.

For thousands of years, people have been tattooing themselves for many reasons. Only in the last few years were increasingly modern techniques used and developed which opened up new opportunities for artistic expression to the artists and therefore, the tattooed. In the last decade, tattoo fashions have experienced unimaginable evolution and momentum because the elites (artists, athletes and musicians), partially excessively, are using the tattoo as self-expression. Tattoos are becoming increasingly more colourful, larger and more artistic. Coloured pigments are also being utilised for beautification, lip augmentation, permanent make-up and scalp micropigmentation.

In the last few years, you might have also spotted some new fashions. There has long been a trend in the industry to replace an unwanted, or rather a non-professionally made, tattoo with another. Equally as often, a small part of a tattoo or permanent make-up will be completely or partially corrected. A further market is the removal of so-called 'Dark Spots', colloquially referred to as sunspots or liver spots.

Consequently, there is a great need for tattoo removal procedures. Different removal techniques are known.

Dermabrasion is already an aged technique, which nevertheless had to be performed by a doctor up until a few years ago. In the process, the skin (epidermis and dermis to several millimeters deep) is removed layer by layer with mostly technical implements or with a surgical raspatory. In addition to the healthy skin, affected tissue is also removed.

The skin abrasions resulting from the removal rarely heal up without extensive scarring. In some cases the skin has to be sewn back together which leaves behind obvious surgical scars.

During the excision, residues in the skin area are excised by way of a surgical operation performed by doctors. This way, larger areas can also be removed. It has to be healthy skin that is taken from another part of the body, partly through additional operations, to be used at this point. In the process, the skin is cut open deeply as part of an operation, which leads to a clearly visible and often extensive scar.

By far, the most commonly used tattoo removal method today is by laser. In the course of this, a split second focussed light energy is shot onto the skin that breaks the residues into small fragments but leaves the tissue undamaged. This happens because the high-energy light, which has to be matched exactly to the absorption spectrum for the residue, triggers an explosion effect. The high energy causes them to explode and could heat the residues very quickly up to 900°. The small particles which are left behind (predominantly nanoparticles) are either pressed into a deeper layer of skin, are absorbed by the lymph or blood system and carried away, or they remain less visible, because they are smaller, situated in the layers of the skin until the next treatment, when they are exploded again and once more made smaller.

Laser is of limited suitability for the removal of tattoos and requires years of experience and lots of specialist knowledge. Many parameters of the equipment have to be in alignment for correct treatment. Laser treatment can lead to skin reddening, and sometimes also severe pain, blister formation and crusty areas. It can create burn scars, hypertrophic scars and keloids. Through the heat build-up, partially carcinogenic new chemical bonds emerge from the ink molecules. Through the shredding of the dye pigments to nanoparticles, medically dangerous impurities get into the lymph and blood systems, the extent and severity of whose negative side effects on the health of the skin and the entire organism are as yet not fully researched.

For many decades, tattooists and beauticians have experimented with the removal of liver spots and tattoos with creams that contain various ingredients. These are administered as a lotion or paste. Through repeated use, dermal applications of the product should lead to a washed out appearance that eliminates the pigment's stain. However, significant removals of tattoos are therefore barely possible because the various layers of the skin act as a sufficiently solid barrier, that substances can hardly penetrate, but, equally as unlikely, that substances can leave the body through the undamaged skin.

In U.S. Pat. No. 8,663,162, a tattoo removal method is described, during which a tattoo removal device is used that introduces lactic acid with a pH less than 1 into the skin with a needle. In the treatment, up to 10 ml of removal fluid is sent from an automatic pump into the needle and directed into the skin opening. An eschar-inducing material is used as a removal fluid.

The company, Tattoo Vanish® Inc., from Las Vegas, USA, removes tattoos through bleaching. Here, the skin is opened to a depth of several millimeters using a micropigmentation device and a salt solution is applied which leads to portions of the ink particles being expelled. The pain of the method is reduced by the use of an anaesthetic. In every case, multiple sessions are necessary for treated sites in order for the bleaching of the tattoo not to appear visible to the eye.

All previously (see above) described, effective methods of tattoo removal, or so-called 'Dark Spots' have the disadvantage that the skin must be broken to some depth, so that the dermis, specifically the growth area of the skin, the stratum papillare, can be broken. Depending on the treatment, or type of treatment, the possibility of keloids or hypertrophic scar development is increased.

SUMMARY

The object of the development was to avoid the previously described disadvantages.

To solve this object, a method for the removal of tattoos and skin alterations is suggested. The invention is based on the knowledge that a principal trigger for the creation of scars is the depth of the invasiveness. The less damaged or irritated the skin is, the fewer propensities there is for scar or keloid creation.

According to an aspect of the invention, the removal fluid is introduced through the small, partial removal of the epidermis. This can happen with a pigmentation device (e.g., a removal device) or with a knife (e.g., a raspatory). Since the removal fluid is merely introduced above the stratum papillare, breaking the dermis is avoided.

By removing such a small area of the epidermis trough-shaped dots are formed which are moistened by the removal fluid. The removal fluid drips and glides out of the open epidermis and mixes with the exiting wound fluid. The removal fluid penetrates from there into the dermis, where the tattoo-ink molecules to be removed are found.

Further developments of the method according to the invention can be understood from the following description and appended claims.

This disclosure also relates to a removal liquid. The removal liquid as per the invention may be available in an encapsulated form (liposomal capsule).

BRIEF DESCRIPTION OF THE DRAWING

In the following, the invention is explained in more detail, with reference to accompanying drawings. Herein shows:

FIG. 1 is a cross section through the skin with epidermis and dermis in which the tattoo ink or other pigmentation is found.

DETAILED DESCRIPTION

As is apparent from FIG. 1, the human skin features multiple layers arranged on top of each other. On the topside, the epidermis 10 is found, which has a thickness of 0.3-1 mm. The epidermis 10 is above a thin layer of skin 11 (stratum basale) that is responsible for the regeneration of epidermis 10 skin cells and is separate from the dermis 12. In the dermis 12, the tattoo forming ink particles 13a, 13b are introduced.

During the removal method according to the invention, the epidermis 10 above a tattoo is removed using a micropigmentation device and a maximum of three circular needles in an area of 0.5-0.8 cm in a round or oval shape, through which so-called dots are formed. That way, the skin is only slightly irritated and the underlying dermis, as well as the connecting tissue is loosened. The needle is directed in circular, constantly moving rotations, a maximum of 3-4 times per dot for around 10-15 seconds to the outer edge of the dot, with very little pressure. The frequent changeover means that the epidermis is also removed in the centre of the so-called dots (treatment areas).

Through a maximum of three applications of the micropigmentation device and the even horizontal orbits of the needle, the skin is carefully removed depending on the shape of the tattoo using oval or round dots. The frequency of the needle, at just 150 stiches per second, is rather gentle in comparison with professional tattoo equipment, which operates with up to 800 stitches per second. The penetration depth of the needle is set using a manual adjustment on the removal device and is on average 0.3-0.5 mm, depending on the body part. A safety device prevents deeper penetration.

By dipping the removal needle in the removal fluid to wet the needle, such as after every application (3-4 times), the treatment area will be only lightly wetted with the removal fluid. The amount of removal fluid used on average per dot may be from about 0.02 ml to about 0.5 ml. In some preferred implementations, the amount used may be about 0.04 ml. The fluid drops and glides through the open epidermis into the ink-bearing dermis and mixes, as well as dilutes itself with the abundance of exiting wound fluid. After every application of the micropigmentation device, the spot is dried with a sterile swab and is cleaned through a short wipe with moderate pressure. A safety distance of at least 8 mm is left between two treatment areas (dots). A maximum of 15-20 dots can be set out, but on average it is only 6-8 dots.

Although this embodiment is described with specific reference to removal of the epidermis with a pigmentation device, a knife or other device, such as a raspatory may also be used. Similarly to the embodiment described above, the raspatory may also be wetted between applications.

The difference with previous methods is above all, that there is no penetration or breaching of the dermis with the method according to the invention. Furthermore, the special removal method in the described manner means that the cell layers in the dermis slacken and the connective tissue is more penetrable. The epidermis that is only partially permeable to liquids is removed, and the cell walls of the dermis are more flexible and allow, after the loosening of the connective tissue, the specially formulated removal fluid to penetrate the outer cell walls, into the ink molecules and balls found in different layers of the dermis.

Tattoo ink can be found in the dermis at depths of up to 4 mm, but even deeper with non-professionally made tattoos.

In this respect, the procedure is clearly less invasive in comparison with a tattoo, even if the procedure leaves a small wound on the outside, similar to a slight abrasion that heals easily.

The present method is based on a combination of the special removal process (see above) by which only a small area of the epidermis is removed, where the conjunctiva (dermis) is made more permeable through slackening and the specially formulated removal fluid with liposomically encapsulated agents can therefore penetrate deeply. Liposomes are small hollow spheres (vesicles), whose coverings or shells are made from one or more phosphatidylcholine lipid bilayers. In the liposomal cell body, other, mostly water-soluble agents can be encapsulated, protected and transported in the skin. Liposomes merge with the barrier layers of the skin and offload the encapsulated agents there. This locally increases the permeability of the barrier layer membranes and the agents can pass. In some embodiments of this disclosure, membranes of the liposomes may be less than about 500 nanometers in diameter.

This enables the gentle penetration of multiple cell layers of the dermis, in which the tattoo ink can be found and that sheds as a result. The shedding happens because of the specific structure of the removal fluid. In the macrophage layer surrounding the ink molecules, it causes an immediate replacement of the macrophages' ink molecules. Since the skin is in repair mode because of the removal of the epidermis, whereby, among other things, all of the necrotic and inorganic components are repelled to the skin's surface, the ink pigments of the tattoo that have only just been discovered by the body, independent of their characteristics, are immediately repelled and sent to the skin's surface where they are bonded into the form of scabs.

Summary of the Individual Steps:

Through the exclusive removal of the epidermis, and the massage action of the removal method, the underlying dermis/conjunctiva is not damaged, but rather made more penetrable.

The specially formulated removal fluid gets through the cell layers of the dermis to the dispersed ink molecules and separates them from the macrophages without destroying or dissecting the cell structure.

Liposomes aid the removal fluid and allow it to more extensively penetrate the deeper situated sites in which the ink molecules can be found. Through this only fairly invasive method, the full or partial destruction of the stratum papillare is avoided, e.g. as is common with surgical procedures. A side effect is that through the gentle, only slightly invasive skin opening of the procedure, the process itself creates virtually no visible scarring.

In the way described, the removal fluid causes the macrophages, which have prevented the tattoo ink from being recognised as foreign bodies in the skin through complete encapsulation until this point, to break away from the ink molecules and immediately repel the recently recognised foreign bodies from the body by way of wound healing and bind fully into a scab on the skin's surface.

The special consistency and formulation of the removal fluid is absorbed into the body for the intended effect on the tattoo as part of a metabolism to glucose so that the fluid is taken into the body without any residue.

The creation of liposomal substances is known in the literature and is produced by one of these methods. The composition of the removal liquid may generally include about 10 to about 80% by weight, and more preferably in some embodiments, 20%-50% by weight, bleach acid. The bleach acid may include hydrochloride, sodium hypochlorite, boric acid, sodium sulphite ($Na_2SO_3$) or sodium dithionite ($Na_2S_2O_4$), hydrogen peroxide, β-hydroxy carboxylic acid, salicylic acid, AHA-acids (α-hydroxy carboxylic acid), or a mixture of one or more of the foregoing.

Listed below are Formulations A-D that have been found to be appropriate removal fluid formulations. In these listings, an approximate weight-percentage (wt.-%) of each component is present. Each listed weight-percentage should be understood to include the term "about" before the numerical value.

| Formulation A | |
|---|---|
| 1) Phosphatidylcholine (saturated) | 06.00 wt.-% |
| 2) α-Hydroxy Carboxylic Acid | 40.00 wt.-% |
| 3) Magnesium 12 Hydroxy Stearate | 02.00 wt.-% |
| 4) Glycerol | 1.00 wt.-% |
| 5) Acetylcholine | 2.00 wt.-% |
| 6) Water | Balance to 100% |

| Formulation B | |
|---|---|
| 1) Phosphatidylcholine (saturated) | 12.00 wt.-% |
| 2) α-Hydroxy Carboxylic Acid | 30.00 wt.-% |
| 3) Substance P | 03.00 wt.-% |
| 4) Alcohol | 6.00 wt.-% |
| 5) Water | Balance to 100% |

| Formulation C | |
|---|---|
| 1) Phosphatidylcholine (saturated) | 05.00 wt.-% |
| 2) Glycolic Acid | 15.00 wt.-% |
| 3) Lactic Acid | 09.00 wt.-% |
| 4) TCA Trichloroacetic Acid | 02.00 wt.-% |
| 5) Sodium Chloride | 05.00 wt.-% |
| 6) Distilled Water | Balance to 100% |

| Formulation D | |
|---|---|
| 1) Phosphatidylcholine (saturated) | 06.00 wt.-% |
| 2) Glycolic Acid | 15.00 wt.-% |
| 3) Lactic Acid | 07.00 wt.-% |
| 4) TCA Trichloroacetic Acid | 02.00 wt.-% |
| 5) Sodium Chloride | 05.00 wt.-% |
| 6) Medium Chain Triglycerides (MCT) | 01.50 wt.-% |
| 7) Allantoin | 00.50 wt.-% |
| 8) Distilled Water | Balance to 100% |

The invention claimed is:

1. A method for removal of tattoos or skin discoloration, the method comprising:
 applying from about 0.02 ml to about 0.5 ml of a removal fluid to a pigmentation device to form a wetted pigmentation device, the wetted pigmentation device comprising one or more needles; and
 with the wetted pigmentation device, forming a treatment area by contacting the one or more needles to an epidermis while traversing a path defining a circumference a maximum of 3 to 4 times in about 10-15 seconds to remove at least a portion of the epidermis bounded by the circumference,
 wherein the removal fluid from the wetted pigmentation device enters the treatment area during the forming the treatment area.

2. The method according to claim 1, wherein the removal fluid is encapsulated in liposomes and the removal fluid is transported by the liposomes, at the treatment area, into an upper dermis.

3. The method according to claim 1, further comprising setting a penetration depth of the one or more needles through a manual adjustment.

4. The method of claim 3, wherein the penetration depth is about 0.3 mm to about 0.5 mm.

5. The method of claim 1, wherein the removal fluid is introduced at an upper dermis and reaches a subcutis by way of a release of liposomes.

6. The method of claim 1, wherein the removal fluid exists in an encapsulated form.

7. The method of claim 6, wherein the removal fluid exists in one or more liposomal capsules.

8. The removal fluid of claim 7, wherein membranes of liposomes comprising the one or more liposomal capsules are less than 500 nanometers in diameter and shells of the one or more liposomal capsules are made of one or more shells.

9. The method of claim 1, wherein the removal fluid includes from about 10% wt. to about 80% wt. bleach acid.

10. The method of claim 9, wherein the bleach acid comprises at least one of hydrochloride, sodium hypochlorite, boric acid, sodium sulphite ($Na_2SO_3$) or sodium dithionite ($Na_2S_2O_4$), hydrogen peroxide, β-hydroxy carboxylic acid, salicylic acid, or AHA-acids (α-hydroxy carboxylic acid), or a mixture thereof.

11. The method of claim 9, wherein the removal fluid includes from about 20% wt. to about 50% wt. bleach acid.

12. The method of claim 1, wherein the treatment area comprises a round or oval shape having an area that is from about 0.5 cm to about 0.8 cm across.

13. A method of removing pigmentation from skin, the skin comprising an epidermis, a stratum basale beneath the epidermis, and a dermis beneath the stratum basale, the method comprising:
 applying a removal fluid to one or more needles;
 causing the one or more needles to move along a path defining a circumference; and
 contacting the one or more needles to the epidermis to remove at least a portion of the epidermis bounded by the circumference to form a treatment area, the one or more needles penetrating the epidermis at a depth less than a thickness of the epidermis to avoid penetrating the stratum basale and the dermis,
 wherein the removal fluid applied to the one or more needles is transferred from the one or more needles into the treatment area and mixes with wound fluid present in the treatment area, and
 wherein the contacting the one or more needles to the epidermis comprises contacting the one or more needles and traversing the path a maximum of 3 to 4 times in about 10-15 seconds.

14. The method of claim 13, wherein the treatment area comprises a first treatment area, the method further comprising forming a second treatment area spaced from the first treatment area.

15. The method of claim 14, wherein the second treatment area is spaced from the first treatment area by about at least 8 mm.

16. The method of claim 13, wherein the one or more needles move in a direction substantially parallel to a central axis of the path.

17. The method of claim 16, wherein the one or more needles move in the direction substantially parallel to the central axis at a frequency of about 150 stitches per second.

18. The method of claim 16, wherein the removal fluid includes from about 10% wt. to about 80% wt. bleach acid, and the bleach acid comprises at least one of hydrochloride, sodium hypochlorite, boric acid, sodium sulphite ($Na_2SO_3$) or sodium dithionite ($Na_2S_2O_4$), hydrogen peroxide, β-hydroxy carboxylic acid, salicylic acid, or AHA-acids (α-hydroxy carboxylic acid), or a mixture thereof.

* * * * *